United States Patent [19]

Lahourcade et a

[11] 4,054,669

[45] Oct. 18, 1977

[54] PHENOLIC MENTHENE DERIVATIVES, THERAPEUTIC COMPOSITION CONTAINING SAME AND THEIR USE AS THERAPEUTIC COMPOSITIONS

[75] Inventors: Bernard Lahourcade, Vielle-Saint-Girons; Christiane Hirigoyen, Saint-Vincent-de-Tyrosse; Maurice Joullie, St-Germain-en-Laye; Gabriel Maillard, Paris; Lucien Lakah, Paris; Christian Warolin, Paris, all of France

[73] Assignees: Les Derives Resiniques et Terpeniques, Dax; S.A. Joullie International, Neuilly-sur-Seine, both of France

[21] Appl. No.: 646,200

[22] Filed: Jan. 2, 1976

[30] Foreign Application Priority Data

Jan. 15, 1975 France .................................. 75.01139

[51] Int. Cl.² .................. A01N 9/00; A01N 9/12; A01N 9/24; A01N 9/26
[52] U.S. Cl. .......................... 424/315; 260/505 C; 260/620; 424/346
[58] Field of Search ............. 424/346, 315; 260/505, 260/621 R

[56] References Cited

U.S. PATENT DOCUMENTS

| 3,524,003 | 8/1970 | Reinert et al. | 424/346 |
|---|---|---|---|
| 3,800,051 | 3/1974 | Barnhart et al. | 424/346 |
| 3,867,466 | 2/1975 | Endou et al. | 260/621 R |

*Primary Examiner*—Albert T. Meyers
*Assistant Examiner*—D. W. Robinson
*Attorney, Agent, or Firm*—Young & Thompson

[57] ABSTRACT

1-Hydroxy-4-(3'-m.menthen-4'-yl)-benzene, 1-hydroxy-3-methyl-4-(3'-m.menthen-4'-yl)-6-isopropyl-benzene and their sulfonates have antiviral activity against influenza virus and antibacterial activity against gram-positive bacteria.

5 Claims, No Drawings

PHENOLIC MENTHENE DERIVATIVES, THERAPEUTIC COMPOSITION CONTAINING SAME AND THEIR USE AS THERAPEUTIC COMPOSITIONS

This invention relates to new phenolic menthene derivatives, and to their therapeutic applications.

This invention relates to compounds having the formula:

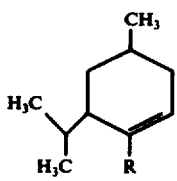

(I)

in which R represents a phenol or thymol residue attached at para-position to the hydroxy group, and their sulfonated derivatives.

As the new compounds of this invention may exist as the cis and trans forms, the invention includes within its scope both such forms and the various mixtures thereof.

The compounds of this invention include particularly 4-(3'-m.menthen-4'-yl)-phenol (referred to hereinafter as m.menthene-phenol) having the formula:

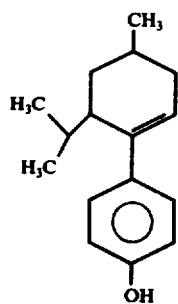

(II)

and its sulfonated derivatives, and 4-(3'-m.menthen-4'-yl)-thymol (referred to hereinafter as m.menthene-thymol) having the formula:

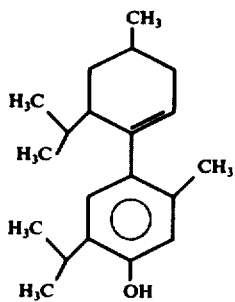

(III)

and its sulfonated derivatives.

The particular structure of such compounds was established in particular using the spin uncoupling N.M.R. and mass spectrographic data.

The invention relates also to a process for the preparation of the above-mentioned new compounds, comprising reacting $\Delta_2$-carene having the formula:

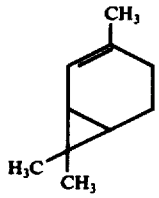

(IV)

with phenol or thymol, to give a compound of the formiula (I) which, if desired, is subsequently sulfonated.

The reaction is advantageously carried out in the presence of a boron trifluoride ether complex, at a temperature below about 50° C.

The sulfonation is effected in a manner known per se, typically with a mixture of sulfuric acid and acetic anhydride.

This reaction is quite novel because it was unexpected to be able to attain such a configuration from any simple terpenic molecule. For example, from sylvestrene, which exhibits a metamenthadiene configuration, fixation of a phenol results in an addition at one or both of the double bonds.

This invention includes also within its scope a therapeutic composition having in particular an antibacterial and antiviral activity, comprising, as active ingredient, a phenolic menthene derivative such as defined above, together with a therapeutically administrable vehicle.

In view of their higher water-solubility, the derivatives are preferably used as alkali metal sulfonates, particularly as the sodium sulfonate.

The following non limiting examples are given to illustrate the process for the preparation of the compounds of this invention.

EXAMPLE 1

Preparation of m.menthene-thymol and its sodium 2-sulfonate (LJ2128)

1. $\Delta_2$-carene (minimum 95% purity; 100 g) and thymol (230 g) are reacted in a three-necked flask, under a nitrogen atmosphere, in the presence of 0.1 cc boron trifluoride etherate.

The exothermic reaction is maintained at 30°–40° C, if necessary in an ice-water bath, during one hour.

After neutralization with a slight excess of lime to which has been added a decolorizing earth (5%), the resulting material is filtered and distilled in vacuo.

Thus are collected: excess thymol, a small ether fraction (less than 10 g) and about 150 g. m.menthene-thymol. This latter colorless product has a boiling point of 150° C under 3 mm mercury. Its other characteristics are:

$N_D^{20}$ = 1.53; Sp. gr. = 0.985 at 20° C; $\alpha J$ = about +40°, under 10 cm.

2. Concentrated sulfuric acid (60 g) solubilized in acetic acid (about 200 g) is poured into this freshly distilled product, dissolved in a 50:50 acetic anhydride/acetic acid mixture.

The highly exothermic reaction is carefully controlled.

After aboiut 20 hours, the reaction mixture is poured into water (800 cc) and is then extracted with an aliphatic solvent such as gasoline C (a straight-run gasoline fraction distilling within the range from 70° to 100° C and having a specific gravity of 0.700), hexane, gasoline E, and the like.

3. After saponification with 10-15% aqueous potassium hydroxide of the m.menthene-thymol present, 80-100 g m.menthene-thymol are recovered from the organic phase, on distillation in vacuo.

4. The aqueous phase is neutralized with an amount of sodium hydroxide corresponding to the amount of sulfuric acid used, the major portion of the acetic acid is distilled off, if required by steam distillation, and the resulting material is neutralized to pH 7.5.

The salted out phase is saponified during one hour, under refluxing conditions, with dilute sodium hydroxide to remove the acetyl derivatives present. The pH is then adjusted to a value below 6, and the material is then made neutral to pH 7.5 with a 10% sodium bicarbonate solution. The desired sulfonate is salted out.

To purify the latter, this salting out step is repeated twice in a concentrated sodium chloride sodium, at a rate of about 100 g aqueous sulfonate in 150 g brine.

Finally, this salted out product is distilled with a water trap, with toluene or hexane, to remove the water and to permit the subsequent precipitation of the sodium chloride which is insoluble in the hot.

After removal of the salt, the solution is cooled and, thus, precipitates as a filterable gel consisting of the sulfonate.

A second treatment with hexane makes it possible, after evaporating off the solvent, to recover the dry and pure m.menthene-thymol-2-sulfonate.

This product is obtained as a white powder which is soluble in physiological saline solution, giving a clear solution.

Thin-layer chromatography over silica gel G (Eluent: 3 parts acetic acid/1 part cyclohexane. Development: spraying with a sodium carbonate solution and with a solution of 1% potassium permanganate and sodium carbonate) gives a spot at Rf = 0.57. The sulfur content is 7.4%.

EXAMPLE 2

Preparation of m.menthene-phenol and its sodium 2-sulfonate (LJ2148)

1. Using the procedure described in Example 1, $\Delta_2$-carene (100 g) is treated with phenol (200 g).

The product is rapidly filtered because it discolors on exposure to light, and is then distilled to recover a large unreacted reusable phenol fraction.

The undistilled material is poured into a 80:20 aqueous-alcoholic solution containing 5% sodium hyddroxide, to give the sodium salt and thus permit extraction with an aliphatic solvent such as hexane, gasoline E, andd the like.

About 35 g phenol ether are recovered from the extracted acidified and neutralized organic solution, after repeated washing and distillation.

The aqueous-alcoholic phase is in turn made acidic, after which the product salted out is washed with water, neutralized and distilled, to give about 50 g m.menthene-phenol.

This product is highly sensitive to light and air; it distils at 135° C/3 mm mercury. It exhibits the other following characteristics:

$N_D^{25}$ = 1.539; Specific gravity = 0.978 at 25° C; J = +14° under 10 c,.

2. The m.menthene-phenol is sulfonated as described for the thymol derivative (see Example 1).

The organic extraction phase gives valueless undeterminable materials.

The aqueous phase is neutralized, salted out and treated as described in Example 1, with saturated salt solutions.

After azeotropic distillation with a water-trap, the product is separated from the salt by dissolution in acetone and is then precipitated from its solution by addition of hexane or pentane.

The sodium m.menthene-phenol-2-sulfonate is obtained as a slightly colored powder, soluble in physiological saline solution.

Its thin-layer chromatography, effected as described in Example 1, gives a single spot of Rf = 0.55.

The sulfur content is 7.7%.

The results of a toxicological and pharmacological investigation, showing in particular the antibacterial and antiviral activity of the compounds of this invention, are given below.

I -Toxicity

Acute toxicity was determined by the intravenous and oral routes, using the Karber and Behrens method, in mice female IFFA-CREDO weighing 20 g (10 mice per dosage level).

The following results were obtained:

TABLE I

| Product | LD$_{50}$ (mg/kg) | |
|---|---|---|
| | I.V. route | Oral route |
| LJ 2128 | 125 | 1925 |
| LJ 2148 | 305 | 2900 |

II - Pharmacological investigation

1. Determination of antibacterial activity

The tests were carried out according to the dilution method.

To determine the activity against Staphylococcus, Proteus vulgaris, Klebsiella pneumoniae and Escherichia coli, use was made of Difco bacto-peptone medium, and nutrient broth T was used to investigate the activity against Pneumococcus.

LJ 2128 and LJ 2148 are active against gram-positive germs, as evidenced by the following Table, LJ 2148 being particularly active against Diplococcus pneumoniae.

| | LJ 2128 | LJ 2148 |
|---|---|---|
| *Staphylococcus pyogenes aureus* Oxford | 140 γ/ml | 28 γ/ml |
| *Streptococcus pyrogenes* 5625 | 16 γ/ml | 10 γ/ml |
| *Diplococcus pneumoniae* 692 | 12 γ/ml | 3 γ/ml |
| *Proteus vulgaris* | >1000 γ/ml | >1000 γ/ml |
| *Klebsiella pneumoniae* | >1000 γ/ml | >1000 γ/ml |
| *Escherichia coli* | >1000 γ/ml | >1000 γ/ml |

2. Determination of the antiviral activity against influenza virus, A$_2$ Hong Kong strain a. Investigation of the growth of influenza virus by inoculation of embryonated eggs 11 Day embryonated eggs, from Leghorn hens, are inoculated by the allantoid route with 100 50% infecting doses of A$_2$ Hong Kong influenza virus.

It is thus possible to determine the threshold dosage of product affecting the viral growth, either preventively or curatively, by assay according to the hemaglutination technique.

After 48 hours incubation at 34° C, the growth rate of the virus is controlled by determination of the hemaglutination rate of the allantoic liquid of the treated eggs and of the control eggs.

Hemaglutination is effected by contacting erythrocytes from chicken embryos with successive dilutions of the allantoic liquids taken from each eggs under sterile conditions.

In one of the tests carried out, the allantoic liquid of the eggs which has received the control viral suspension exhibited a hemaglutinating activity at the average level of 1/640.

The allantoic liquids of the eggs which had been administered 0.5 mg LG 2128 or 0.5 mg LJ 2148 ½ hour prior to the viral injection did not agglutinate the erythrocytes.

Thus, derivatives LJ 2128 and LJ 2148 possess a total inhibiting activity against the growth of influenza virus when the products are injected prior to inoculation of the virus. Only partial activity is obtained when the injection is given subsequently to inoculation of the virus.

b. Investigation of in vivo antiviral activity in mice

During an influenza epidemic, contagion from man-to-man occurs on inhalation of the vesicles carried by the aerial route and carrying the influenza virus.

The surface cells of the nasal epithelium are the primary locus of viral growth. This justifies the direct application of an antiviral drug in the nasal cavity, either by instillation or by aerosol inhalation.

One of the conventional methods for screening drugs active in vivo against influenza virus comprises making mice inhale a virus aerosol preparation and then treating the mice with the test material by the same route and using the same test procedure.

To determine the efficiency of the test materials, two parameters are taken into account:

the percent surviving mice, after a definite period of time (e.g., 12 days);

the mean survival time, together with criteria such as observation of the systemic condition of the mice, determination of the viral growth at the pulmonary level, and the like.

It was found that the changes in the weight curve of the mice reflected their systemic condition in an excellent manner and, thus, was an additional criterion of the activity of the test materials.

The experimental device used comprises an aerosol generating apparatus and a chamber in which the mice are placed in lots of 10. The test material and viruis aerosols are administered simultaneously. For this purpose, a Y-shaped tube is connected with the inlets to the chamber.

According to another procedure, the test material is administered at periods of time other than the time at which the virus is inoculated, i.e., 1 hour, 2 hours, 6 hours, hours, 24 hours, 48 hours and during five days eithert prior or subsequently to administration of the virus, to evaluate a potential preventive or curative effect.

The rate of flow of the apparatus is such as to administer at each aerosol treatment step about 1/20 of the intravenous $LD_{50}$ of the product to each mice.

The infectant dose of the virus kills in average 90% of the mice within 12 days ($LD_{90}$).

Controls for the tolerance to the product are effected under similar conditions.

On the other hand, activity control tests were effected with antiviral substances such as cyclooctylamine hydrochloride or amantadine hydrochloride.

The following results were obtained with LJ 2128 and LJ 2148.

TABLE II

Weight change and percent survival of mice treated with LJ 2128 and LJ 2148 aerosols administered once and simultaneously with an aerosol of influenza virus, $A_2$ Hong Kong strain (Each product is administered at a dosage of about 1/20 of intravenous $LD_{50}$; the dosage of influenza virus is about $LD_{90}$).

The Table gives the average daily weights (g) of the lots of mice, the daily number of fatal issues and the number of mice which survive on the 12th day following viral inoculation.

|  | Control virus | LJ 2128 + virus | Control virus | LJ 2128 + virus | Control virus | LJ 2148 + virus |
|---|---|---|---|---|---|---|
|  | 20.5 g | 20.5 g | 20.5 g | 20.5 g | 20.3 g | 20.4 g |
|  | 20.8 g | 20.9 g | 20.8 g | 20.5 g | 20.2 g | 20.8 g |
|  | 19.7 g | 20.4 g | 20.4 g | 20.6 g | 15.6 g | 19.3 g |
|  | 17.8 g | 20.1 g | 18.7 g | 19.6 g | 15.2 g | 20.1 g |
|  | 17.8 g | 20.1 g | 18.7 g | 20.6 g | 14.1 g | 19.5 g |
|  | 15.2 g 1 fatal issue | 17.9 g | 16.2 g | 19.6 g | 13.5 g 4 fatal issues | 18.9 g |
|  | 15.7 g 7 fatal issues | 17.8 g | 15.7 g 2 fatal issues | 19.7 g | 15 g 5 fatal issues | 19.6 g |
|  | 16 g | 18.4 g | 17.5 g 6 fatal issues | 20.2 g | — 1 fatal issue | 20.4 g |
|  | 19.5 g 1 fatal issue | 19.1 g | 18 g | 20.3 g |  | 21.3 g |
|  | 20 g | 19.3 g | 19.5 g | 20.6 g |  | 21.4 g |
|  | 20 g | 19.3 g | 20 g | 21.4 g |  | 21.6 g |
|  | 20.5 g | 20.8 g | 20 g | 21.5 g |  | 21.6 g |
| Mice surviving on the 12th day (lots of 10 mice) | 1 | 10 | 2 | 10 | 0 | 10 |

The simultaneous administration of a LJ 2128 or LJ 2148 aerosol and of an influenza virus aerosol prevents the development of viral pneumonia in mice infected with $A_2$ Hong Kong strain influenza virus.

Indeed (see Table II) all the treated mice are found to survive whereas the death rate of the control infected mice is very high and corresponds to a $LD_{90}$.

The changes in weight and in the systemic condition of the mice treated with LJ 2128 and LJ2148 are more satisfactory than in the case of mice administered amantadine or cyclooctyalmine.

III - Therapeutic applications

In view of their antimicrobial and antiviral properties against influenza virus, the compounds of this invention may be used in the local or systemic treatment of respiratory conditions in children and adults.

As anti-infectious agents, their antimicrobial properties are selectively active against Gram-positive germs, particularly against streptococcus and pneumococcus. In view of the frequent combination of the influenza viral infection and of the microbial infection, the antiviral properties of the compounds of this invention make them useful in the treatment of conditions having a mixed etiology.

The antibacterial activity of said compounds justifies their use in the treatment of acute or subacute respiratory conditions of infectious nature and, in many cases, makes antibiotherapy unnecessary or shortens its use.

The compounds are predominantly applicable :

in pneumology: for the treatment of influenza, acute and chronic bronchitis, broncho-pneumonosea and viral diseases of the lungs. For the treatment of childreen; in cases of respiratory involvement of infectious diseases which occur in childhood.

in otohinolaryngology: for the treatment of pharyngitis, rhino-pharyngitis, amygdalitis, stomatitis, sinusitis, rhinopharyngeal involvements of bacterial conditions of of influenza virus conditions.

The compounds may be administered by the oral, rectal, nasal and parenteral routes.

The average daily dosage regimen in man is between 0.75 g and 1.50 g. In children, the daily dosage regimen is calculated as a function of the body weight, on the basis of about 0.02 g per kg body weight.

The compounds of this invention may be used as various pharmaceutical forms such as tablets, capsules, syrups, suppositories, nasal drops, aerosols, injectable, solutions, and the like, the active ingredient being combined with a therapeutical administrable vehicle.

In pharmaceutic compositions, the compounds may be combined with compounds capable of reinforcing, modifying or completing the therapeutic activity (e.g., they may be combined with antihistaminic, antitussive, antipyretic, mucolytic and like compounds).

Examples of pharmaceutic compositions are given below:

EXAMPLE 3

| Tablets | |
|---|---|
| LJ 2148 | 0.200 g |
| Sucrose | 0.020 g |
| Corn starch | 0.030 g |
| Colloidal silica | 0.020 g |
| Magnesium stearate | 0.005 g |
| for a final tablet weighing | 0.275 g |

EXAMPLE 4

| Syrup (for adults) | |
|---|---|
| LJ 2148 | 2.5 g |
| Sucrose | 70 g |
| Methyl p-hydroxybenzoate | 0.15 g |
| Flavor | q.s. |
| Distilled water, q.s. to make | 100 ml |

Example 5

| Suppositories (for children) | |
|---|---|
| LJ 2128 | 0.150 g |
| Semi-synthetic glycerides, q.s. for 1 suppository weighing | 2 g |

Having now described our invention what we claim as new and desire to secure by Letters Patent is:

1. A compound selected from the group consisting of 1-hydroxy-4-(3'-m.menthen-4'-yl)-benzene, 1-hydroxy-3-methyl-4-(3'-m.menthen-4'-yl)-6-isopropyl-benzene and their sulfonates.

2. 1-hydroxy-4-(3'-m.menthen-4'-yl)-benzene, and its sodium sulfonate.

3. 1-hydroxy-3-methyl-4-(3'-m.menthen-4'-yl)6-isopropyl-benzene, and its sodium 2-sulfonate.

4. Therapeutic composition having antiviral activity against influenza virus and antibacterial activity against gram-positive bacteria comprising a therapeutically effective amount of a compound as claimed in claim 1, together with a therapeutically administrable carrier.

5. A process for the treatment of patients suffering from influenza viral infection or gram-positive bacterial infection comprising administering to said patients a therapeutically effective amount of a compound as claimed in claim 1.

* * * * *